(12) United States Patent
Ziegelmann et al.

(10) Patent No.: US 9,326,507 B2
(45) Date of Patent: May 3, 2016

(54) **PHEROMONE COMPOSITION FOR TREATING *VARROA* MITE INFESTATION**

(71) Applicant: Universitaet Hohenheim, Stuttgart (DE)

(72) Inventors: Bettina Ziegelmann, Stuttgart (DE); Peter Rosenkranz, Tuebingen (DE)

(73) Assignee: Universitaet Hohenheim, Stuttgart (DE)

( * ) Notice: Subject to any disclaimer, the term of this patent is extended or adjusted under 35 U.S.C. 154(b) by 0 days.

(21) Appl. No.: 14/420,461

(22) PCT Filed: Aug. 6, 2013

(86) PCT No.: PCT/EP2013/066485
§ 371 (c)(1),
(2) Date: Feb. 9, 2015

(87) PCT Pub. No.: WO2014/023733
PCT Pub. Date: Feb. 13, 2014

(65) Prior Publication Data
US 2015/0196028 A1    Jul. 16, 2015

(51) Int. Cl.
*A01N 37/06* (2006.01)
*A01K 51/00* (2006.01)
*A01N 37/02* (2006.01)
*A01N 63/02* (2006.01)

(52) U.S. Cl.
CPC .............. *A01N 37/06* (2013.01); *A01K 51/00* (2013.01); *A01N 37/02* (2013.01); *A01N 63/02* (2013.01)

(58) Field of Classification Search
CPC ........ A01N 37/06; A01N 37/02; A01K 51/00
USPC .......................................................... 514/549
IPC ...................... A01N 37/06, 37/02; A01K 51/00
See application file for complete search history.

(56) References Cited

U.S. PATENT DOCUMENTS

| 5,135,758 A | 8/1992 | Arnold et al. |
| 2007/0196415 A1 | 8/2007 | Chen et al. |

FOREIGN PATENT DOCUMENTS

WO     9842815     10/1998

OTHER PUBLICATIONS

Hansen et al. "Free Fatty Acid Content of Cacao Beans Infested with Storage Fungi" (1973) J. Agr. Food Chem. 21(4): 665-670.
Rozenkranz et al. "Biology and Control of Varroa destructor" (2010) J. Invertebrate Pathol. 103:S96-S119.
Diploma thesis of Bettina Ziegelmann, University of Hohenheim, Oct. 2008 Title: Regulation of the copulation behaviour of the bee mite Varroa destructor by scents of the female.

*Primary Examiner* — Kristin Vajda
(74) *Attorney, Agent, or Firm* — Lewis Kohn & Walker LLP; David M. Kohn; Kari Moyer-Henry

(57) ABSTRACT

A composition and method for treating a *Varroa* mite infestation using a sexual pheromone for disrupting the mating behavior of the *Varroa* mite. Additionally, a pesticide for applying to a mating place of the *Varroa* mite for disrupting the mating behavior of the *Varroa* mite.

14 Claims, 5 Drawing Sheets

PHEROMONE COMPOSITION FOR TREATING *VARROA* MITE INFESTATION

This application is a U.S. National Stage Application claiming the benefit of priority under 35 U.S.C. 371 from International Patent Application No. PCT/EP2013/066485 filed Aug. 6, 2013, which claims the benefit of priority from European Patent Application Ser. No. EP 12179905.0 filed Aug. 9, 2012, the entire contents of which are herein incpororated by reference.

FIELD OF THE INVENTION

The invention concerns the use of a composition comprising a *Varroa* mite sexual pheromone for disrupting the mating behaviour of the *Varroa* mite. The invention further concerns a method for treating a *Varroa* mite infestation comprising providing a composition comprising a *Varroa* mite sexual pheromone, and applying the composition to a mating place of the *Varroa* mite for disrupting the mating behaviour of the *Varroa* mite. In addition, the invention concerns a pesticide for controlling a *Varroa* mite infestation comprising at least two *Varroa* mite sexual pheromones.

BACKGROUND OF THE INVENTION

The bee mite *Varroa destructor* is one of the biggest threats for apiculture world wide. The ectoparasite was introduced into Europe from Asia in the 1970s where it shifted from its natural host, the Eastern honeybee *Apis cerana*, to the European honeybee *Apis mellifera*. *Apis mellifera* turned out to be particularly sensitive to the ectoparasite such that *Varroa destructor* successfully spread throughout the entire world within a few decades. The only country, which was so far spared from *Varroa destructor*, is Australia. Consequently, hardly any bee colonies exist nowadays, which are free of *Varroa destructor*.

*Varroa destructor* infestations significantly afflict honeybee colonies causing losses of up to 30% during hibernation. Without treatment, honeybee colonies infested by *Varroa destructor* die within two to three years. Overall, *Varroa destructor* is believed to considerably contribute to the dying of bee colonies, which is observed throughout the entire globe.

To control *Varroa* mite infestation primarily liquid compositions of various chemicals are used, including synthetic acaricides, organic acids and essential oils. Common synthetic acaricides are based on organophosphate coumaphos, pyrethroides, tau-fluvalinate, flumethrin or amitraz. Most of these pesticides are easy to apply and convenient in practice, because they do not required refined knowledge of the mites' biology. They posses, however, considerable disadvantages, since most of the synthetic acaricides are lipophilic substances and are therefore absorbed by the bees' wax where they accumulate over time. This can harm the bees, which are continuously exposed to increasing amounts of multiple compounds stored in the wax. Moreover, the chemicals can pollute the honey and other bee products, as already observed with residues of synthetic acaricides exceeding the European Union maximum limit in various honeybee products. Additionally and most importantly, synthetic acaricides were found to create resistances of the *Varroa* mites, leading to unrecognized failure of control in the field and serious damage of beekeeping. Organic acids and essential oils used for *Varroa* control include formic acid, oxalic acid, lactic acid and thymol. Formic acid is the most extensively used, since it is the only acaricide, which is able to kill mites within sealed brood cells. Organic acids and essential oils, in general, have a low risk of accumulating in bee products. They show, however, substantial disadvantages in their handling and application. Lactic acid and oxalic acid, for example, have to be applied under broodless conditions and thus are only suitable for colonies kept in regions with a brood stop during winter. In addition, the efficiency of some compounds depends on the climatic conditions outside as well as inside the bee hive, e.g. the evaporation pressure within the colony, such that the efficiency of these acaricides is difficult to control. In general, for most organic acids and essential oils, the range between their efficiency regarding parasite extinction and their toxicity for the host is particularly narrow, such that the effects of these substances are often variable and unreliable.

Therefore, an efficient treatment of *Varroa* infestation is needed which allows an easy application and handling while preventing undesired side effects on bee colonies and their products.

SUMMARY OF THE INVENTION

In a first aspect, the invention is directed to the use of a composition comprising a *Varroa* mite sexual pheromone for disrupting the mating behaviour of the *Varroa* mite, wherein the sexual pheromone is selected from the group consisting of oleic acid, ethyl oleate, palmitic acid, ethyl palmitate, stearic acid, ethyl stearate and a mixture thereof.

In a second aspect, the invention is directed to a method for treating a *Varroa* mite infestation, comprising
  providing a composition comprising a *Varroa* mite sexual pheromone, and
  applying the composition to a mating place of the *Varroa* mite for disrupting the mating behaviour of the *Varroa* mite,
  wherein the sexual pheromone is selected from the group consisting of oleic acid, ethyl oleate, palmitic acid, ethyl palmitate, stearic acid, ethyl stearate and a mixture thereof.

In a further aspect, the invention is directed to a pesticide for controlling a *Varroa* mite infestation comprising at least two *Varroa* mite sexual pheromones, wherein the sexual pheromone is selected from the group consisting of oleic acid, ethyl oleate, palmitic acid, ethyl palmitate, stearic acid and ethyl stearate.

DETAILED DESCRIPTION

In a first aspect, the invention is directed to the use of a composition comprising a *Varroa* mite sexual pheromone for disrupting the mating behaviour of the *Varroa* mite, wherein the sexual pheromone is selected from the group consisting of oleic acid, ethyl oleate, palmitic acid, ethyl palmitate, stearic acid, ethyl stearate and a mixture thereof.

The lifecycle of *Varroa* is closely linked to its honeybee host and does not have a free living stage (Rosenkranz et al., 2010). The entire reproduction cycle of *Varroa* mites, including mating and laying eggs, takes place within a sealed honeybee brood cell. For successively reproducing, a *Varroa* female mite enters the brood cell with the host lava, and subsequently starts oogenesis. The offspring matures and mates within the limited time of honeybee brood development. Any female offspring, which was not inseminated when the bee leaves the brood cell, cannot contribute to the further reproduction, because it cannot generate fertilized eggs. In fact, it is believed that these females, as well as the males die once the bee hatches.

Figure 1:
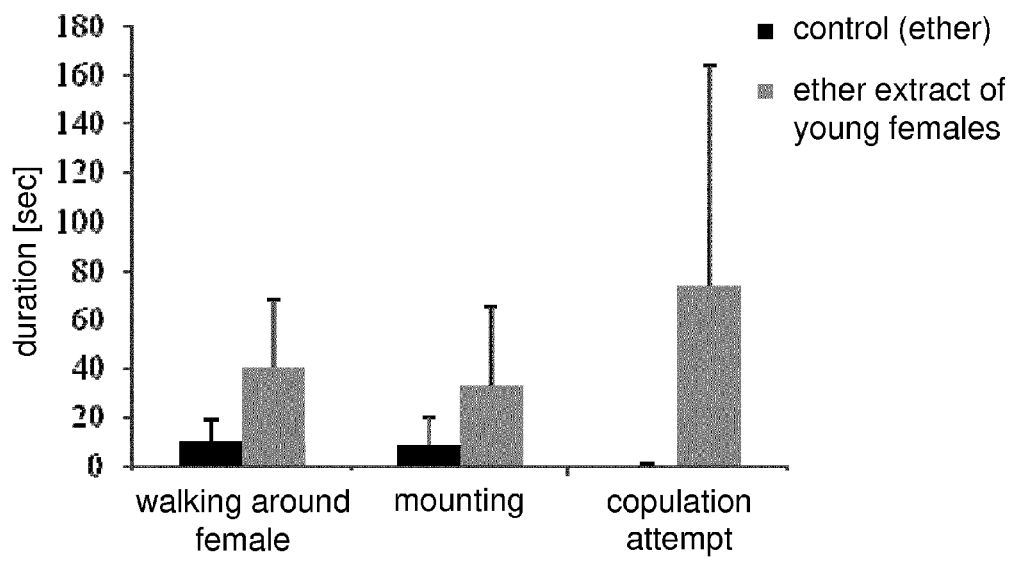
FIG. 1 shows the response of males of *Varroa destructor* to a female deutochrysalis in the presence of diethyl ether extracts of freshly moulted females.

It was observed that *Varroa* females preferably parasite nurse bees in order to be transported to unsealed brood cells. After entering the brood cell, the mite starts oogenesis and generates up to six egg cells in sequence. The first egg is unfertilized and thus gives rise to a haploid male *Varroa* mite. The subsequently generated eggs are fertilized and develop into female *Varroa* mites. During development, the *Varroa* mites pass proto- and deutonymphal stages including mobile as well as immobile phases, with the later referred to as proto- and deutochrysalis, respectively. The developing mites feed at the bee pupa developing in the brood cell. Immediately after reaching adulthood, the mites are fertile and mate. In this regard, it was observed that the male mite always mates with the youngest of the sequentially generated females, but does hardly show any attempt to mate with a not yet fertile female, e.g. a deutochrysalis, or with an already inseminated female. The inventors now found that this behaviour is controlled by sexual pheromones released by young adult *Varroa* females. The term "sexual pheromone", as used herein, refers to a chemical substance, which causes an animal to change its sexual behaviour when exposed to the substance. The inventors could reveal the functions of sexual pheromones for *Varroa* mite mating by preparing extracts from young fertile females and applying samples of the extracts to a deutochrysalis. Although *Varroa* males usually do not approach a deutochrysalis, they show mating behaviour towards a deutochrysalis treated with the extract of fertile females (FIG. 1). To further reveal the chemical nature of the behaviour inducing substance, the inventors separated the extract into a pentane and an ether fraction. Since only the ether fraction triggered mating behaviour of *Varroa* males (FIG. 2), the contents of this fraction were further analyzed. Surprisingly, the extract only contained three different fatty acids and their respective ethyl ester: oleic acid, ethyl oleate, palmitic acid, ethyl palmitate, stearic acid and ethyl stearate. Moreover, the inventors found that not only the mixture of these compounds but also each compound itself could trigger mating behaviour of a *Varroa* male towards a deutochrysalis (FIG. 3), with oleic acid showing the most prominent effect. Thus, each of the identified sexual pheromones as well as a mixture thereof is suitable to induce *Varroa* mite mating behaviour.

Figure 5:
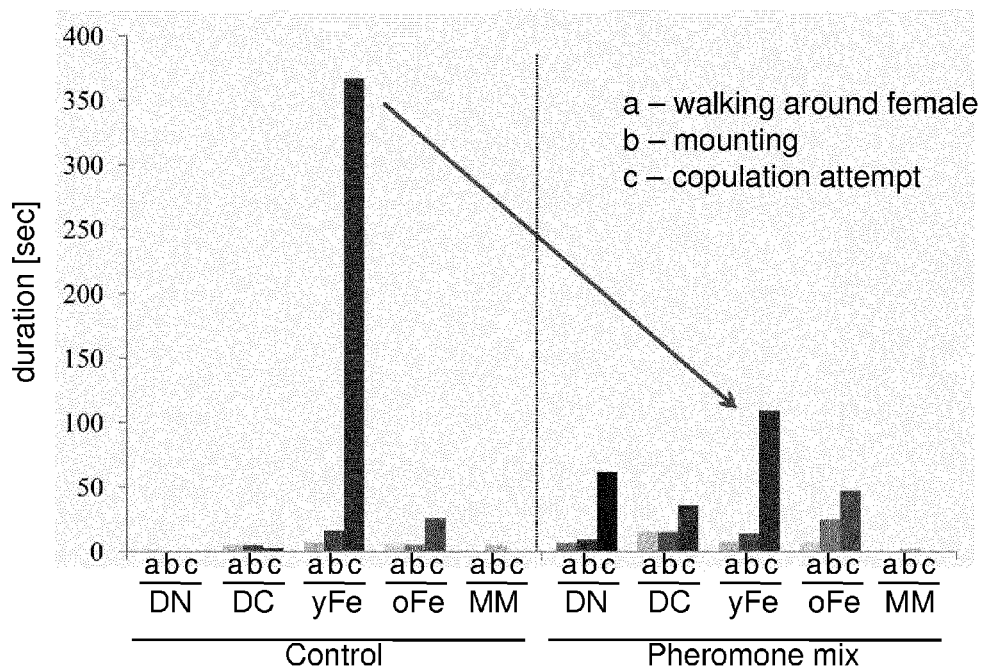
FIG. 5 shows the behaviour of males of *Varroa destructor* towards deutonymphe (DN), deutochrysalis (DC), young female (yFe), old female (oFe) and the mother mite (MM) in the absence (control) and the presence of a pheromone mix comprising palmitic acid, ethyl palmitate, oleic acid, ethyl oleate, stearic acid and ethyl stearate.

Following this, the inventors additionally revealed that these compounds, although inducing mating behaviour, are suitable to actually prevent successful mating of *Varroa* mites. Exposing a *Varroa* mite family, including deutonymphe, deutochrysalis, young females, old females, a male and the mother mite, to a mix of sexual pheromones significantly disrupts the mating behaviour of the male (FIG. 5). If sexual pheromones are artificially and ubiquitously present in the mites environment, the attempts of the male to mate with a fertile female is significantly reduced. Simultaneously the male undertakes efforts to mate with infertile or already inseminated females, which normally hardly occurs. This reduces the reproduction success in total. Without to be bound to a specific theory, it is believed that due to the exposure of sexual pheromones, the male mite is no longer able to distinguish between a young and thus fertile female and a non-fertile or already inseminated female. In consequence, the male mite spends considerable time with approaching females that cannot contribute to the reproduction of the population. When distributing the pheromones throughout the brood cell, the male mite might even be attracted by any other object present in the honeybee brood cell. Since the entire reproduction cycle has to be completed within the brood cell before the hatching of the bee, the total number of fertilized females per reproduction cycle is all the more reduced, the more time the *Varroa* male spends mating infertile or already inseminated females. This significantly decreases the overall reproduction success of *Varroa* mites. Thus, the sexual pheromones identified by the inventors are suitable to disrupt *Varroa* mite mating behaviour and provides an efficient tool to inhibit *Varroa* mite infestation.

In addition, all of the identified compounds are naturally occurring fatty acids, which even form a common part of a mammal's diet. Thus, none of these compounds is expected to be harmful or display major side effects. Consistently, oleic acid, palmitic acid and stearic acid are all exempted from the requirement of a tolerance when used in agriculture practice, in particular when used as ingredients in pesticide formulations. Moreover, since these compounds are ubiquities in nature, they are biodegraded, reducing their accumulation and thus the risk of side effects due to increasing concentrations of the compounds.

In a preferred embodiment of the invention, the composition is used in apiculture. Honeybees are the most important host for *Varroa* mites, with registered losses of up to 30% of bees during hibernation due to *Varroa* infestation.

In a preferred embodiment, the composition is applied to a bee hive, preferable to a brood comb of the bee hive. In apiculture, bees are kept in artificial nesting sites, so-called bee hives. Nowadays, motile bee hives are most common as e.g. Langstroth hives, which can be moved according to the blossom of different honey plants. Additionally, the Langstroth hive comprises frames into which the bees build their honeycombs and which can be easily removed from the hive to harvest honey and bees' wax. The hives further include specific chambers, so-called brood chambers, comprising the brood combs, where the queen lays the eggs and the larvae develop. This is also the site of *Varroa* mite reproduction and development. Therefore, applying the composition to the bee hive or even to the brood combs directly ensures that the composition reaches the site of *Varroa* mite reproduction and efficiently disrupts the mating behaviour of the mites.

In a preferred embodiment, about 1 µg to about 10 µg, preferably about 2 µg to about 7 µg, more preferred about 5 µg of the sexual pheromone is applied per $cm^2$ brood comb surface. For efficiently interfering with the mating behaviour of the *Varroa* mites, males should be exposed to concentrations of pheromones similar or exceeding those released by young and fertile *Varroa* females. If the concentration of the sexual pheromones applied to the brood combs is less than those released by the females, the males might still be able to distinguish the fertile females and thus successfully mate.

In a preferred embodiment, the composition is applied by spraying, is integrated into bees' wax or is applied continuously, preferably by a dispenser. Applying fluids to the bee hive by spraying is an easy technique commonly used by beekeepers, inter alia for applying conventional acaricides. Thus, for applying the sexual pheromone by spraying, the composition can be purchased in suitable spray bottles or may be applied using already available equipment. This allows the immediate introduction of the application of the composition into already established beekeeping processes. Besides that, the composition is particularly preferred to be introduced into bees' wax. The identified sexual pheromones are all lipophilic substances and can thus be easily mixed with and taken up by the wax. During the beekeeping process, old bees' wax is repeatedly removed from the hive and cleaned by treatment with heat and water. This wax is used for manufacturing bee wax products, but also for providing new honeycomb foundations of the bee hive. The composition can be easily introduced into the fluid wax after cleaning and before casting the new foundations. Once the foundations are reintroduced into the bee hive and used as brood combs, the sexual pheromones are immediately at the site of *Varroa* mite reproduction. If the composition is integrated into the wax, preferably about 10 mg to about 100 mg, more preferred about 20 mg to about 75 mg, even more preferred about 50 mg of the sexual pheromone is added per kg bees' wax. These concentrations are suitable for providing the sexual pheromone within the brood comb, in concentrations that efficiently disrupt *Varroa* mating behaviour. Applying the composition continuously has the advantage that the concentration of the sexual pheromones within the bee hive remains constant. Since the sexual pheromones are biodegradable compounds, their concentration decreases over time. Thus, to ensure an efficient reduction of *Varroa* mite population throughout the entire season, application by a dispenser is particularly advantageous. In addition, the dispenser automatically delivers the composition without the need of opening the bee hive and disturbing the bee colony. Likewise, using a dispenser, the composition can be applied without adding further working steps for the beekeeper. This increases handling convenience and reduces the overall working effort, both considerable issues for beekeeping, which particularly in Europe is mostly carried out as part time work or in spare time.

In a preferred embodiment, the *Varroa* mite is *Varroa destructor, Varroa underwoodi, Varroa rindereri* or *Varroa jacobsoni*. Although other *Varroa* mites are known to infest honeybee colonies, *Varroa destructor* is the most important honeybee ectoparasite. The honeybees predominantly used for honey production are most sensitive to *Varroa destructor*, probably due to the lack of a balanced host-parasite relationship, since this ectoparasite was introduced into Europe from Asia. However, since all *Varroa* mites are closely related including genetic and behavioural similarities, the composition is also suitable to impair mating behaviours of other *Varroa* mite besides *Varroa destructor*.

In a second aspect, the invention is directed to a method for treating a *Varroa* mite infestation, comprising
  providing a composition comprising a *Varroa* mite sexual pheromone, and
  applying the composition to a mating place of the *Varroa* mite for disrupting the mating behaviour of the *Varroa* mite,
wherein the sexual pheromone is selected from the group consisting of oleic acid ethyl oleate, palmitic acid, ethyl palmitate, stearic acid, ethyl stearate and a mixture thereof.

The term "treating", as used herein, includes preventing a *Varroa* infestation of a not yet affected bee colony as well as treating an already infested bee colony. The term likewise refers to inhibiting the growth of a *Varroa* mite population as well as to reducing the overall size of a *Varroa* mite population. Thus, the method may be carried out before or after an infestation has occurred. The method provides an efficient measure for reducing *Varroa* mite infestation, because it impairs the reproduction success of the mites. This in turn improves the bees' survival rate as well as the health of the entire colony, since with reducing the number of *Varroa* mites the number of bee larvae that develops undisturbed increases.

In a preferred embodiment, the *Varroa* mite infestation is an infestation of honeybees, preferably of *Apis mellifera, Apis cerana, Apis koschevnikovi* or *Apis nigrocincta*. Of the known honeybee species, *Apis mellifera* is economically most important, since it is the predominant bee used worldwide for producing honey and further bee products.

In a preferred embodiment, the mating place is a honeybee brood comb. The entire reproduction cycle of *Varroa* mites, including mating, takes place in honeybee brood combs. Thus, by applying the composition directly at the brood comb, the overall amount of composition needed is reduced and the treatment's efficiency improved.

In a preferred embodiment, about 1 µg to about 10 µg, preferably about 2 µg to about 7 µg, more preferred about 5 µg of the sexual pheromone is applied per $cm^2$ brood comb surface.

In a preferred embodiment, applying the composition comprises spraying the composition, distributing the composition by a dispenser or integrating the composition into bees' wax.

In a particularly preferred embodiment, about 10 mg to about 100 mg, preferably about 20 mg to about 75 mg, more preferred about 50 mg of the sexual pheromone is integrated per kg bees' wax.

In a further aspect, the invention is directed to a pesticide for controlling a *Varroa* mite infestation comprising at least two *Varroa* mite sexual pheromones, wherein the sexual pheromone is selected from the group consisting of oleic acid, ethyl oleate, palmitic acid, ethyl palmitate, stearic acid and ethyl stearate. Although each of the identified sexual pheromones itself is suitable for disrupting mating behaviour of *Varroa* mites, a combination of the sexual pheromones was found to be most efficient. When the pesticide is applied to the site of mating of *Varroa* mites, usually brood combs of honeybees, the mites are artificially exposed to high levels of sexual pheromones during the process of mating. Since the male mite relies on the sexual pheromones to identify fertile females, the application of the pesticide reduces the probability of successful mating and thus the male's reproductivity. Thereby, the growth of the entire *Varroa* population is inhibited, keeping the population constant or even decreasing the total number of mites with each generation. Thus, the pesticide provides an efficient tool for treating *Varroa* mite infestation.

In a preferred embodiment, the pesticide comprises about or more than 70% oleic acid, about or more than 9% ethyl oleate, about or more than 10% palmitic acid, about or more than 2.5% ethyl palmitate, about or more than 3.5% stearic acid and/or about or more than 5% ethyl stearate. When analyzing the extracts derived from fertile young *Varroa* females, the inventors found that the individual sexual pheromones are present in specific concentrations. Applying a composition at concentrations which are equal or higher than those released by young *Varroa* females, disables the male to distinguish different females, probably even to distinguish *Varroa* mites from any other object in the brood comb. Thereby, the composition substantially disturbs the *Varroa* mite mating behaviour, reducing the chance of successful mating to random. Therefore, the pesticide provides an efficient tool for inhibiting *Varroa* mite infestation.

EXAMPLES

1. Materials and Methods
1.1 Collection of Mites

Male and female *Varroa* mites were obtained from brood combs of heavily infested *Apis mellifera* colonies at the Apicultural State Institute, University of Hohenheim in Germany. Sexually mature males and freshly molted adult females as well as female deutochrysalis were collected from brood cells 8 to 9 days after capping. Female deutochrysales and freshly molted adult female mites were transferred into queen cell cups (Nicot System®, Karl Jenter, Metzingen) and kept at 28-30° C. for a maximum of 2 hours in order to prevent a decrease in vitality and mobility.

1.2 Extraction of Female *V. destructor*

Extracts were prepared in screw-top vials by immersing about 20 young freshly molted female mites, which have been found to be attractive in the bioassay, in diethyl ether (stabilized with ethanol) for two weeks. Per individual, 5 µl of the respective solvent was used. After two weeks the extracts were transferred in new vials and stored at −20° C. until use.

1.3 Fractionation of Extracts with Column Chromatography

Ether extracts of young attractive females were fractionated on a silica gel micro column. Dry silica gel (0.25 g; Silica gel 60, 0.06-0.2 mm) was suspended with pentane in a test tube. After pouring the slurry into the column, the silica gel was washed with 10 ml pentane. The female extracts were evaporated to 5 µl and filled up with 195 µl pentane. The extract was then pipetted on top of the column and eluted sequentially with 2 ml pentane and 2 ml ether. The obtained pentane and ether fractions were evaporated to a concentration of 1 female mite equivalent per 5 µl and stored at −20° C. until use.

1.4 Mating Bioassays

The responses of male *Varroa* mites to extracts, fractions, and pure substances were measured by using the "mating bioassay": total extracts, fractions and pure substances were applied to a piece of filter paper (size: 1.5 mm×15 mm) with a 10 µl Hamilton syringe. The filter paper was folded in the middle and placed at the edge of the plastic cell cups (Nicot System®, Karl Jenter, Metzingen, 9 mm inner diameter) that served as a test arena. A living female deutochrysalis was placed at the bottom of the cell cup at 3.5 mm distance to the filter paper. This immobile ontogenetic stage has been demonstrated to be completely non-attractive to the male mite and was therefore used as a dummy. After three tests, the dummies were replaced by new ones. The male responses towards the deutochrysalis were categorized as follows: (1) movement towards/around the deutochrysalis and palpating it, (2) mounting the dorsum of the deutochrysalis and (3) copulation attempts on the venter of the deutochrysalis. The duration of each of these behaviours was recorded over a period of 5 minutes using the Observer 2.0 software (Noldus Information Technology). All tests were performed at temperatures of 33-34° C. at the bottom of the test arena.

1.5 Bioassays with Total Extracts of Young Females, Fractions of the Extracts and Pure Substances The extract was applied to the filter paper in doses of 2 female equivalents; in control tests the filter paper was treated with ether only. Pentane and ether fractions were tested in concentrations of 5 female equivalents in the same way. The higher concentration was applied in order to equalize possible losses of active substances during the column fractionation. Single substances that were identified from the active fraction (see 2.6) were purchased (Sigma Aldrich, GC grade), dissolved in diethyl ether and were tested in doses of 1 ng, 10 ng, 100 ng and 1000 ng.

1.6 Chemical Analysis

Structural analysis of the volatile compounds were performed on a Shimadzu GC-MS combination (GC-17A/GCMS-QP 5050A) equipped with a split/splitless injector and a fused silica DB-5 column (30 m×0.25 mm I.D. and 0.25 µm film thickness). The analyses were operated with the following conditions: 60° C. isothermal for 2 minutes, followed by a temperature increase to 300° C. at a rate of 4° C./min that was held for 12 min. The temperatures of the injector and detector were 240° C. and 280° C., respectively. For each analysis, 1.5 µl of the extract corresponding to 5 *Varroa* female equivalents were injected. The compounds of the active fraction were identified by analysis of the mass spectra and retention time followed by co-injection of the identified pure substances.

1.7 Data Analysis

Behavioural data were analyzed with the SPSS 15.0 statistics software. One Way ANOVA was performed to evaluate the male response toward the female deutochrysalis while being exposed to total extracts, fractions or pure substances. Differences between groups with $p<0.05$ were considered statistically significant.

2. Results
2.1 Male Responses to Total Extracts of Young Females and Fractions

Male *Varroa destructor* did not show any copulatory responses when they were exposed to deutochrysalis and filter paper treated with solvent. Only few single males mounted the female dorsum or moved to the female's venter for a few seconds, but did not show any clear copulation attempts. In contrast, when males were exposed to filter paper containing the total extract of young females, mounting behaviour and copulation attempts with the deutochrysalis took place, resembling the typical mating behaviour towards young females (FIG. 1). However, in the venter-to-venter position males did not pause at the gonopore area on one side but moved from one gonopore to the other. Male responses were highly significant for all three behavioural categories (walking around female: ANOVA, $p<0.001$, n=30; mounting: ANOVA, $p<0.005$, n=30; copulation attempts: ANOVA, $p<0.001$, n=30). Males spent one-fifth of the test time with copulation attempts.

Figure 2:
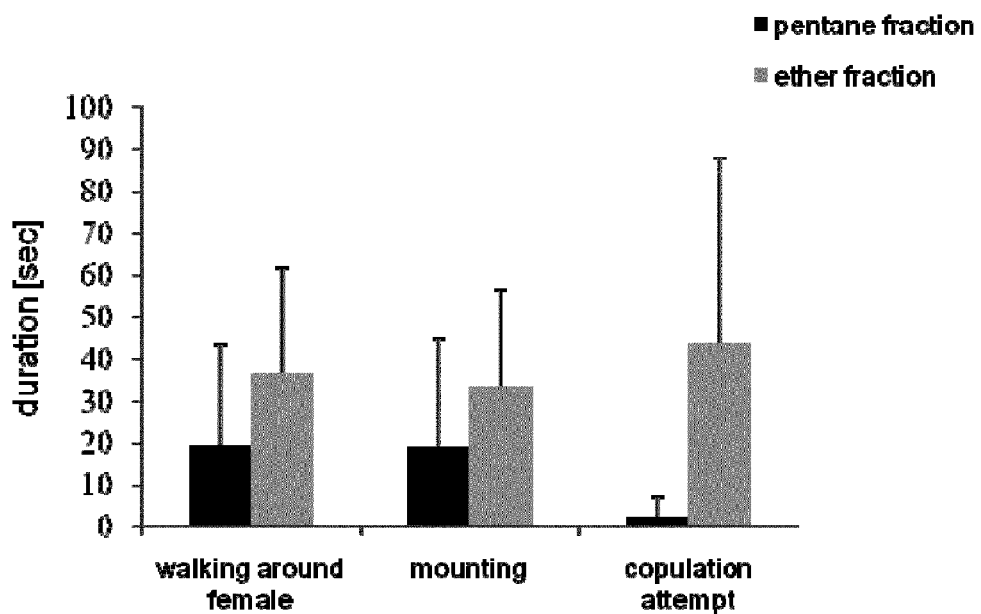
FIG. 2 shows the response of males of *Varroa destructor* to a female deutochrysalis in the presence of the pentane fraction or the ether fraction of diethyl ether extracts of freshly moulted females.

In bioassays with fractions of ether extracts of young adult females, the diethyl ether fraction induced significantly more male mating behaviour for all three behavioural categories than the pentane fraction (FIG. 2; walking around female: ANOVA, $p<0.05$, n=24; mounting: ANOVA, $p<0.05$, n=24; copulation attempts: ANOVA, $p<0.005$, n=24). Thereby, the mean duration of copulation attempts of the ether fraction was comparable to responses observed in the presence of the total extract. In contrast, no clear copulation attempts occurred in the presence of the pentane fraction.

2.2 Chemical Analysis

Figure 4:
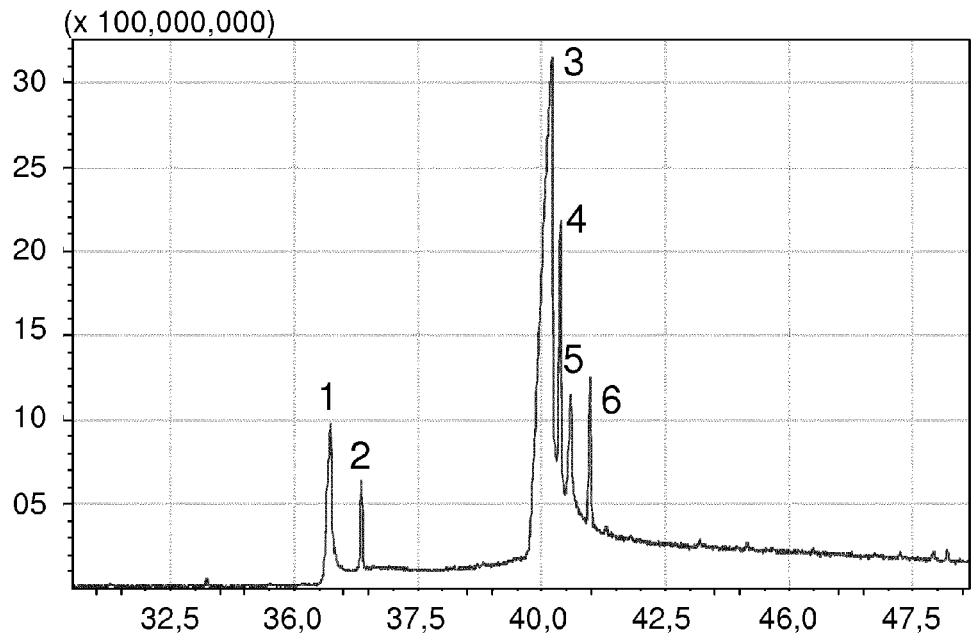
FIG. 4 shows the total ion chromatogram of the diethyl ether fraction of a diethyl ether extract of young females of *Varroa destructor*. The single substances were identified based on their mass spectra and by co-injection with pure substances: palmitic acid (1), ethyl palmitate (2), oleic acid (3), ethyl oleate (4), stearic acid (5) and ethyl stearate (6).

Qualitative GC-MS analysis of the behaviourally inactive pentane fraction revealed a pattern mainly composed of uneven n-alkanes with chain lengths of 21-29 carbon atoms and the respective alkenes and methyl-alkanes. The biological active polar fraction was dominated by the fatty acids oleic acid, palmitic acid, and stearic acid, as well as their respective ethyl esters (FIG. 4). Among these, oleic acid is clearly the main component. Based on the peak area it accounts for approximately 70%. Ethyl oleate and palmitic acid amount for approximately 10% each, and the remaining components ethyl palmitate, stearic acid, and ethyl stearate for less than 5% peak area. All these compounds are derived from the lipid metabolism in arthropods.

2.3 Male Responses to Pure Substances

Figure 3:
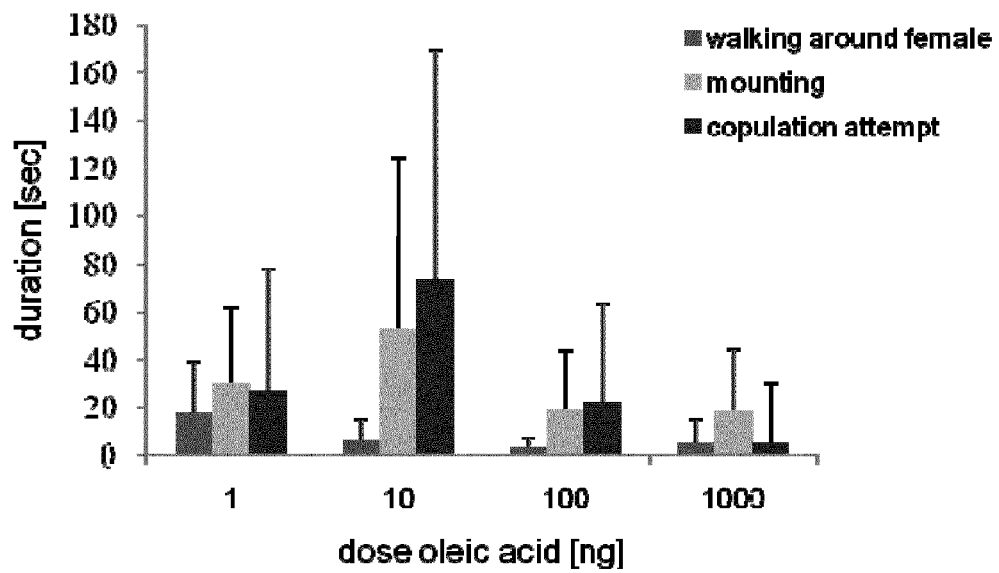
FIG. 3 shows the response of males of *Varroa destructor* to a female deutochrysalis in the presence of single substances, which were identified in the diethyl ether fraction of extracts of young females. The substances were oleic acids (FIG. 3 A), ethyl oleate (FIG. 3 B), palmitic acid (FIG. 3 C), ethyl palmitate (FIG. 3 D), stearic acid (FIG. 3 E), and ethyl stearate (FIG. 3 F).
Figure 3:
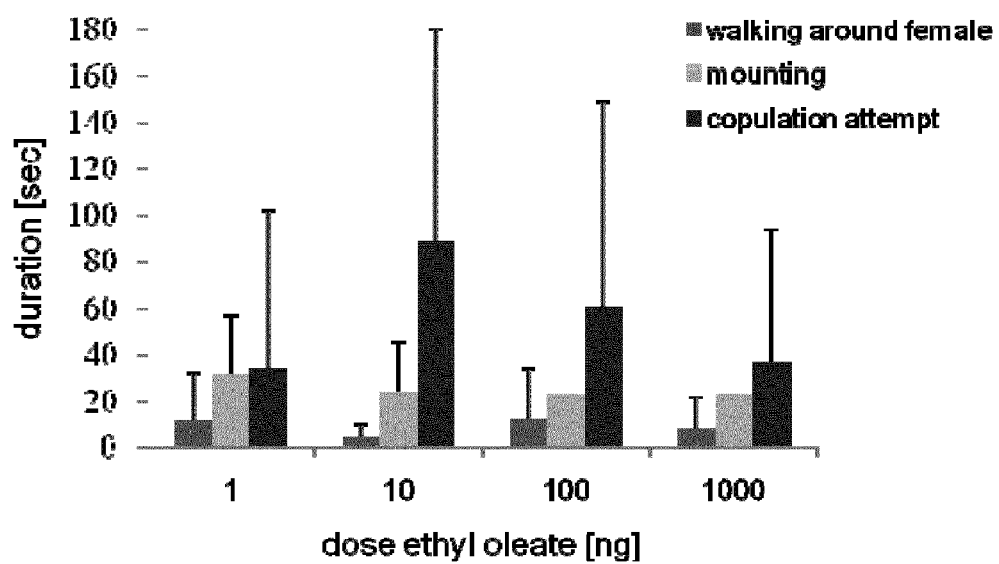
Figure 3:
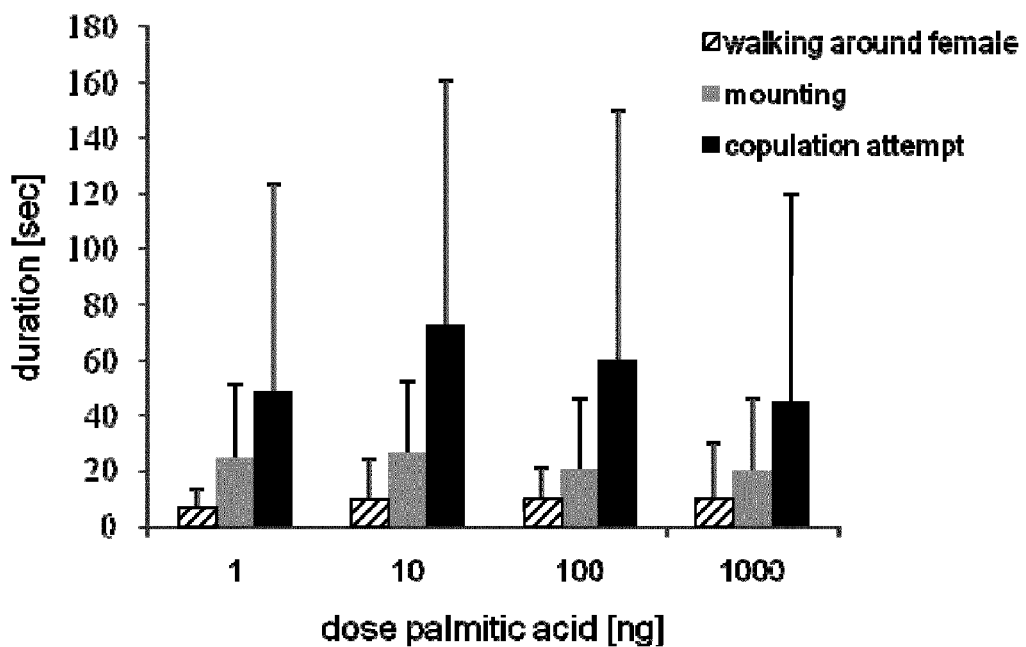
Figure 3:
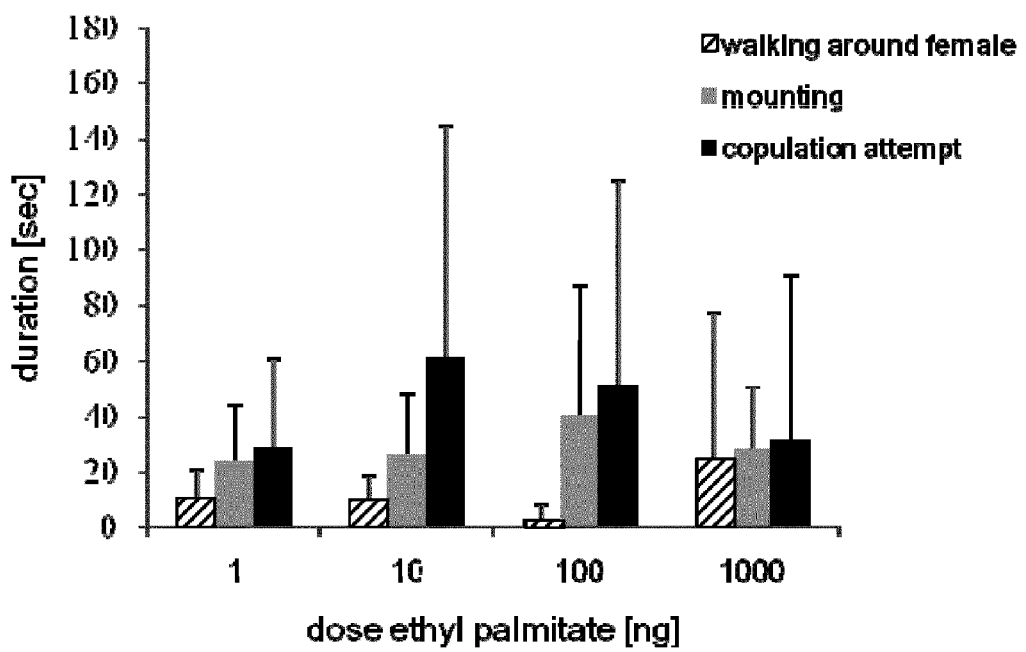
Figure 3:
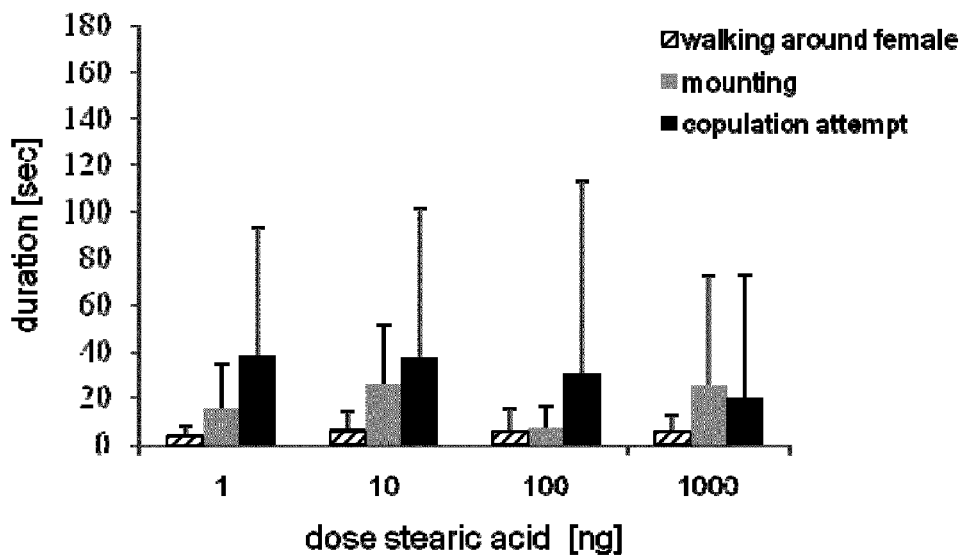
Figure 3:
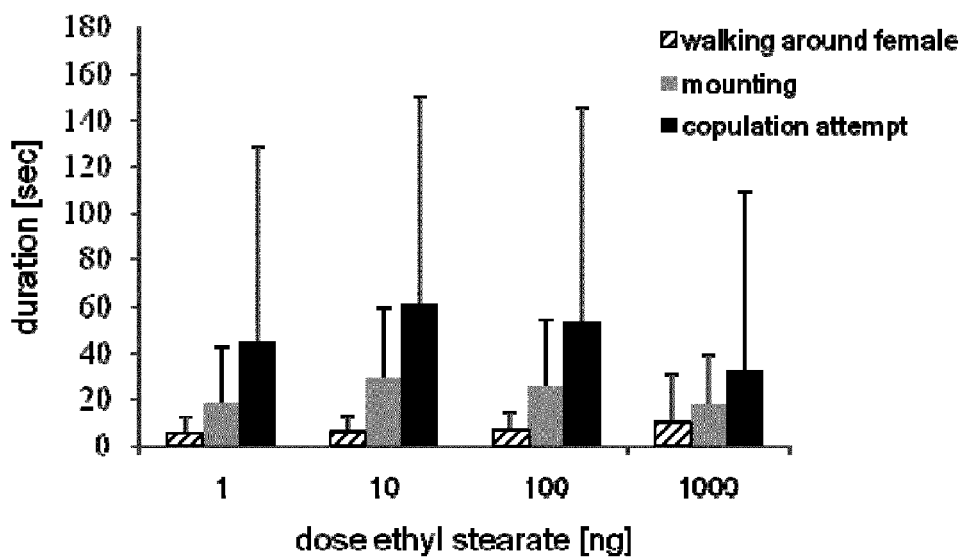

In bioassays with synthetic substances identified in the ether fraction, all fatty acids and fatty acid esters were biological active and elicited the male mating behaviour. Copulatory responses to oleic acid were significantly highest at a dosage of 10 ng and lowest at 1000 ng (FIG. 3 A). For ethyl oleate, the same trend was evident, albeit without significant differences. Palmitic acid, ethyl palmitate, and ethyl stearate also showed maximum copulatory responses at 10 ng and lower responses to other concentrations, but the differences were also not significant (FIG. 3 C, D, F). In bioassays with stearic acid the differences between the copulatory responses to the four dosages were low and the maximal copulation attempts at a dose of 1 ng were lower compared to the other compounds (FIG. 3 E).

In the bioassays, all substances stimulated the male mating behaviour which demonstrates that they are part of the *Varroa* sex pheromone. The highest copulatory responses were observed for the main component, oleic acid. Additionally, a significant dose-dependency with a maximum duration of copulation attempts at 10 ng was found.

2.4 Male Mating Behaviour in the Ubiquitous Presence of the Sex Phermone

In order to evaluate the effect of the sex pheromone on the male behaviour under conditions comparable to the honeybee brood cell, tests with entire "*Varroa* families" matching the natural situation 9 to 10 days after cell capping were performed. These families consisted of one adult male, the mother mite, two daughter mites of different age, one female deutochrysalis as well as one female deutonymph. During the first phase of the experiment the male's behaviour within the mating bioassay was analysed without application of any pheromonal components (control). Thereafter, a mixture of the pure substances (25 ng/μl each) was applied to a filter paper and offered to the test arena. In tests without additional pheromone males showed a clear and significant preference for the youngest adult female, whereas the other female stages were less attractive or not attractive at all. In tests with additional application of the artificial sex pheromone mixture male mites were confused and showed an increased searching behaviour (FIG. 5). Compared to tests without artificial pheromone (i) the males tried to copulate with all female mites regardless of size and stage of maturity and (ii) the duration of copulation attempts with the young adult females were significantly reduced. Therefore, this approach had two effects on the mating disruption of *Varroa* mites: First, the male mite "wasted time" through copulation attempts with non-matured female stages and second, the number and the duration of the copulation attempts with the proper young and mature female were reduced. In addition, by the application of additional pheromone components, the number of successful matings and thus the growth of the *Varroa* population within a bee colony can be reduced.

REFERENCES

Rosenkranz P, Aumeier P, Ziegelmann B., J Invertebr Pathol. 2010 January; 103 Suppl 1:S96-119. Epub 2009 Nov. 11. Biology and control of *Varroa destructor*.

The invention claimed is:

1. A method of using a composition for disrupting the mating behaviour of the *Varroa* mite, the composition comprising a *Varroa* mite sexual pheromone, wherein the sexual pheromone is selected from the group consisting of oleic acid, ethyl oleate, palmitic acid, ethyl palmitate, stearic acid, and ethyl stearate.

2. The method of claim 1, wherein the composition is used in apiculture.

3. The method of claim 2, wherein the composition is applied to a bee hive.

4. The method of claim 1, wherein about 1 μg to about 10 μg of the sexual pheromone is applied per $cm^2$ brood comb surface.

5. The method of claim 1, wherein the composition is applied by spraying, is integrated into bees' wax or is applied continuously.

6. The method of claim 5, wherein about 10 mg to about 100 mg of the sexual pheromone is integrated per kg bees' wax.

7. The method of claim 1, wherein the *Varroa* mite is *Varroa destructor, Varroa underwoodi, Varroa rindereri* or *Varroa jacobsoni*.

8. A method for treating a *Varroa* mite infestation, the method comprising:
  a) providing a composition comprising a *Varroa* mite sexual pheromone, and
  b) applying the composition to a mating place of the *Varroa* mite for disrupting the mating behavior of the *Varroa* mite, wherein the sexual pheromone is selected from the group consisting of oleic acid, ethyl oleate, palmitic acid, ethyl palmitate, stearic acid, ethyl stearate.

9. The method of claim 8, wherein the *Varroa* mite infestation is an infestation of honeybees.

10. The method of claim 8, wherein the mating place is a honeybee brood comb.

11. The method of claim 10, wherein about 1 μg to about 10 μg of the sexual pheromone is applied per $cm^2$ brood comb surface.

12. The method of claim 8, wherein the method of applying the composition comprises spraying the composition, distributing the composition by a dispenser, or integrating the composition into bees' wax.

13. The method of claim 12, wherein about 10 mg to about 100 mg of the sexual pheromone is integrated per kg bees' wax.

14. A pesticide for controlling a *Varroa* mite infestation comprising a single *Varroa* mite sexual pheromone selected from the group consisting of oleic acid, ethyl oleate, palmitic acid, ethyl palmitate, stearic acid, and ethyl stearate.

* * * * *